United States Patent
Li et al.

(10) Patent No.: US 11,354,830 B2
(45) Date of Patent: Jun. 7, 2022

(54) SYSTEM AND METHOD FOR TOMOGRAPHIC IMAGE RECONSTRUCTION

(71) Applicant: The General Hospital Corporation, Boston, MA (US)

(72) Inventors: Quanzheng Li, Boston, MA (US); Georges El Fakhri, Boston, MA (US); Kyungsang Kim, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/320,068

(22) PCT Filed: Jul. 25, 2017

(86) PCT No.: PCT/US2017/043635
§ 371 (c)(1),
(2) Date: Jan. 23, 2019

(87) PCT Pub. No.: WO2018/022565
PCT Pub. Date: Feb. 1, 2018

(65) Prior Publication Data
US 2019/0272653 A1    Sep. 5, 2019

Related U.S. Application Data

(60) Provisional application No. 62/366,177, filed on Jul. 25, 2016.

(51) Int. Cl.
*G06T 11/00* (2006.01)
*A61B 6/03* (2006.01)
(Continued)

(52) U.S. Cl.
CPC ............ *G06T 11/006* (2013.01); *A61B 6/032* (2013.01); *A61B 8/13* (2013.01); *A61B 6/037* (2013.01);
(Continued)

(58) Field of Classification Search
None
See application file for complete search history.

(56) References Cited

U.S. PATENT DOCUMENTS 8,160,340 B2 *  4/2012  Vija ........................ G06T 5/002
                                                        382/131
9,478,049 B2 * 10/2016  Bippus .................. G06T 11/005
(Continued)

FOREIGN PATENT DOCUMENTS

WO        2015044237 A1       4/2015

OTHER PUBLICATIONS

Dutta, J. et al. "Quantitative statistical methods for image quality assessment." Theranostics 3.10 (2013): 741.
(Continued)

*Primary Examiner* — Nancy Bitar
(74) *Attorney, Agent, or Firm* — Quarles & Brady LLP (57) ABSTRACT

The present disclosure a system and method for generating a tomographic image of a subject. In some aspects, the method includes receiving an initial image acquired from a subject using the tomographic imaging system, and performing, using the initial image and a cost function model, a penalty calculation based on a spatially variant hyper-parameter. The method also includes generating an updated image using the penalty calculation, and generating a finalized image by iteratively updating the updated image until a stopping criterion is met.

15 Claims, 6 Drawing Sheets

(51) Int. Cl.
*A61B 8/13* (2006.01)
*G16H 30/40* (2018.01)
(52) U.S. Cl.
CPC ........ *G06T 2211/424* (2013.01); *G16H 30/40* (2018.01)

(56) References Cited

U.S. PATENT DOCUMENTS

| | | | |
|---|---|---|---|
| 9,524,567 B1* | 12/2016 | Brokish | A61B 6/5205 |
| 9,558,570 B2* | 1/2017 | Liang | A61B 6/583 |
| 10,868,572 B2* | 12/2020 | Wang | H04B 1/38 |
| 2015/0030227 A1* | 1/2015 | Liang | A61B 6/032 382/131 |
| 2015/0262389 A1 | 9/2015 | Li | |
| 2016/0055658 A1* | 2/2016 | Liang | A61B 6/583 382/131 |
| 2016/0225169 A1* | 8/2016 | Bippus | G06T 11/005 |

OTHER PUBLICATIONS

Fessler, J. A., et al. "Spatial resolution properties of penalized-likelihood image reconstruction: space-invariant tomographs." IEEE Transactions on Image processing 5.9 (1996): 1346-1358.
International Searching Authority. International Search Report and Written Opinion for application PCT/US2017/043635. dated Oct. 20, 2017. 7 pages.

* cited by examiner

SYSTEM AND METHOD FOR TOMOGRAPHIC IMAGE RECONSTRUCTION

CROSS REFERENCE TO RELATED APPLICATIONS

The present application is a U.S. National Stage of PCT Application No. PCT/US2017/043635 filed on Jul. 25, 2017 which is based on, claims priority to, and incorporates herein by reference in its entirety U.S. Provisional Application Ser. No. 62/366,177, filed Jul. 25, 2016, and entitled "SYSTEM AND METHOD FOR TOMOGRAPHIC IMAGE RECONSTRUCTION."

BACKGROUND

The field of the disclosure relates generally to tomographic imaging. More particularly, the present disclosure relates to systems and methods for improved tomographic image reconstruction.

In the fields of medical imaging and security screening, non-invasive imaging techniques have gained importance due to benefits that include unobtrusiveness, ease, and speed. In medical and research contexts, these imaging systems are used to image organs or tissues beneath the surface of the skin. A number of non-invasive imaging modalities exist today. A particular modality may be selected based upon the organ or tissue to be imaged, upon the spatial and/or temporal resolution desired, or upon whether structural or functional characteristics are of interest. Examples of these imaging modalities include positron emission tomography (PET) imaging, single photon emission computed tomography (SPECT) imaging, x-ray computed tomography (CT) imaging, magnetic resonance imaging (MRI), and others.

Typically, tomographic imaging systems measure photon counts of X-ray or Gamma rays from multiple projections, or angles relative to an imaged subject, and use the acquired tomographic data to generate cross-sectional views of the subject. As such, a wide variety of algorithms have been developed to generate, or reconstruct, tomographic images from the acquired data. Depending upon the imaging modality and clinical application, these algorithms exhibit various strengths and weakness. For instance, tomographic image reconstruction using statistical methods can achieve better contrast and signal-to-noise ratio (SNR) compared to more conventional filtered backprojection (FBP) techniques due to an ill-posed reconstruction problem.

Therefore, there is a continuous need for improved systems and methods for tomographic image reconstruction.

SUMMARY OF THE INVENTION

The present disclosure provides a novel approach for tomographic image reconstruction that overcomes the drawbacks of previous technologies, as will become apparent from descriptions below. The systems and methods provided herein can be used in a variety of imaging applications, including medical, security, and others.

In one aspect of the present disclosure, a method for generating an image using a tomographic imaging system is provided. The method includes receiving an initial image acquired from a subject using the tomographic imaging system, and performing, using the initial image and a cost function model, a penalty calculation based on a spatially variant hyper-parameter. The method also includes generating an updated image using the penalty calculation, and generating a finalized image by iteratively updating the updated image until a stopping criterion is met.

In another aspect of the present disclosure, a system for reconstructing a tomographic image of a subject is provided. The system includes an input configured to receive a plurality of images acquired from a subject using a tomographic imaging system, and at least one processor. The processor is configured to receive an initial image acquired from a subject, and perform, using the initial image and a cost function model, a penalty calculation based on a spatially variant hyper-parameter. The processor is also configured to generate an updated image using the penalty calculation, and generate a finalized image by iteratively repeating the calculation until a stopping criterion is met. The system further includes an output for at least displaying the finalized image.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present disclosure is directed to a system and method for tomographic image reconstruction using imaging data. Such data may be acquired as part of a medical imaging process, a security screening process, an industrial analysis process, or other application. Currently, in many reconstruction algorithms, a cost function is minimized in order to generate an unknown image from projection measurements. Since a direct model rarely provides satisfactory solutions, a penalty term, controlled by a fixed parameter, is often introduced. However, such parameter is often chosen manually, and can be very difficult to optimize for real-world variations. This is because the penalty term parameter is highly dependent on the noise level of the measurement, which may not be known a priori. As a result, many scanner vendors provide a parameter table for many noise level cases, and parameter selection is done by visually checking the resulting image. However, the noise level of different voxels in the reconstructed image can be irregular, potentially degrading the image quality and prohibiting uniform convergence.

Therefore, the present disclosure provides systems and methods for tomographic image reconstruction that overcome these problems. In particular, a spatially variant hyper-parameter approach is described herein, whereby a hyper-parameter controlling between the data fidelity and penalty terms is auto-estimated, and tuned in an iterative reconstruction process. This allows for acquiring desirable or even optimal results without relying on post-acquisition analysis by humans, as well as ensuring convergence. In some aspects, performance may be improved by combining a local impulse response function with Fisher information, providing a spatially variant hyper-parameter method.

In many tomographic imaging modalities, such as CT, SPECT, PET, digital tomosynthesis, optical imaging, and others, photon counts of X-ray or Gamma ray are measured. Such photon counts follow Poisson noise distributions. Therefore, to reduce the noise level, a penalty term is often introduced in the cost function used for reconstructing an image, with the general form:

$$\min_x L(x; y) + \beta \Psi(x). \quad (1)$$

In Eqn. 1, $L(x; y)$ is the log-likelihood function of image x by given measurement y, and $\Psi(x)$ is the penalty function. $L(x; y)$ follows the Poisson noise model. $\beta$ represents the hyper-parameter utilized to control the noise level between the $L(x; y)$ and $\Psi(x)$. Conventionally, $\beta$ is a constant that is manually selected.

Most imaging system manufacturers provide a $\beta$-table for many noise cases and allow approximate selection of $\beta$. For instance, noise level can be determined by radiation dose, such as kVp and mAs for CT, or an amount of radiopharmaceutical for PET. However, this may not enough to define the noise level because the patient body size is also a critical factor. Specifically, if a patient's body is bigger, the noise level may be higher under the same scanning condition. Therefore, the exact noise level for each patient may not be a priori measured.

By contrast, in the present approach, a desirable or even an optimal $\beta$ may be decided by the noise level, in an automated fashion by way of an iterative process. For instance, if the noise is high, the optimal $\beta$ is high. More specifically, a spatially variant hyper-parameter may be obtained, and calculated in each iteration of reconstruction. In some aspects, the present method may use Fisher information of the Poisson distribution. The Fisher information of the raw measurement (y) and the re-projection image ($\bar{y}$) may be calculated and compared. In particular, in the Poisson noise model, the Fisher information of the raw measurement and the re-projection image are $$\frac{1}{y} \text{ and } \frac{1}{\bar{y}}.$$

The hyper-parameter $\beta$ may then be obtained as follows:

$$\beta = \frac{A^T\left(A \odot \left(\frac{1}{y} - \frac{1}{\bar{y}}\right)^2\right)}{A^T\left(A \odot \left(\frac{1}{y}\right)^2\right)}. \quad (2)$$

In Eqn. 2, $\odot$ represents the hadamard product operator (point-wise multiplication), A represents the projection operator, and $A^T$ represents the back-projection operator. Additionally, $\bar{y} = Ax^n$, where n is the iteration number, and AI is the projection of identity matrix filled with ones, which can be pre-computed. More than one back-projection ($A^T$) executions may be needed in each iteration.

For a speed up in calculation, Eqn. 2 may be approximated as follows:

$$\beta \approx \frac{A^T\left(A \odot \left(\frac{1}{y} - \frac{1}{\bar{y}}\right)^2 / \left(\frac{1}{y}\right)^2\right)}{A^T(AI)} = \frac{A^T\left(A \odot \left(1 - \frac{y}{\bar{y}}\right)^2\right)}{A^T AI}; \quad (4)$$

$$\beta_j = \frac{\sum_{i=1}^M a_{ij}\left(1 - \frac{y_i}{\bar{y}_i}\right)^2 \left(\sum_{j'=1}^N a_{ij'}\right)}{\sum_{i=1}^M a_{ij}\left(\sum_{j'=1}^N a_{ij'}\right)}; \quad (5)$$

where, $A^T A$ can be pre-computed by calculating $(\sum_{i=1}^M a_{ij})(\sum_{j'=1}^N a_{ij'})$. As appreciated from the above, an additional back-projection execution may be performed in the $\beta$ calculation as compared to conventional reconstruction techniques.

The original update term is as follows:

$$x^{n+1} = x^n - \left(\frac{\dot{L}(x) + \beta \dot{\Psi}(x)}{\ddot{L}(x) + \beta \ddot{\Psi}(x)}\right); \quad (6)$$

where $\dot{D}(x)$ and $\ddot{D}(x)$ denote the first and second derivatives.

Herein, the update equation may be modified using this property:

$$\frac{\dot{L}(x) + \beta \dot{\Psi}(x)}{\ddot{L}(x) + \beta \ddot{\Psi}(x)} \leq \left(\frac{\dot{L}(x)}{\ddot{L}(x)} + \beta \frac{\dot{\Psi}(x)}{\ddot{\Psi}(x)}\right) / (1 + \beta). \quad (7)$$

This means the gradient becomes higher and convergence speed becomes faster. Then, the update term is as follows:

$$x^{n+1} = x^n - \left(\frac{\dot{L}(x)}{\ddot{L}(x)} + \beta \frac{\dot{\Psi}(x)}{\ddot{\Psi}(x)}\right) / (1 + \beta). \quad (8)$$

As appreciated from the above, the hyper-parameter $\beta$ may be estimated in an iterative reconstruction process, for example, by comparing two images from data fidelity term and penalty term, or comparing the fisher information of re-projection and original measurement in each iteration. Therefore, the hyper-parameter is changed in each iteration. To improve performance, a local impulse response function (noise property) may be used, providing a spatially variant hyper-parameter.

In some aspects, the hyper-parameter can be obtained using a normalized back-projection of difference images between Fisher information functions of the original measurement and re-projection data. In another approach, for each iteration, two images of data fidelity term and penalty term can be separately calculated. A hyper-parameter satisfying the condition that the image not to diverge may be selected. The main idea is to update the hyper-parameter in each iteration to keep the distance between the data fidelity term and the penalty term within the convergent range.

Figure 1:
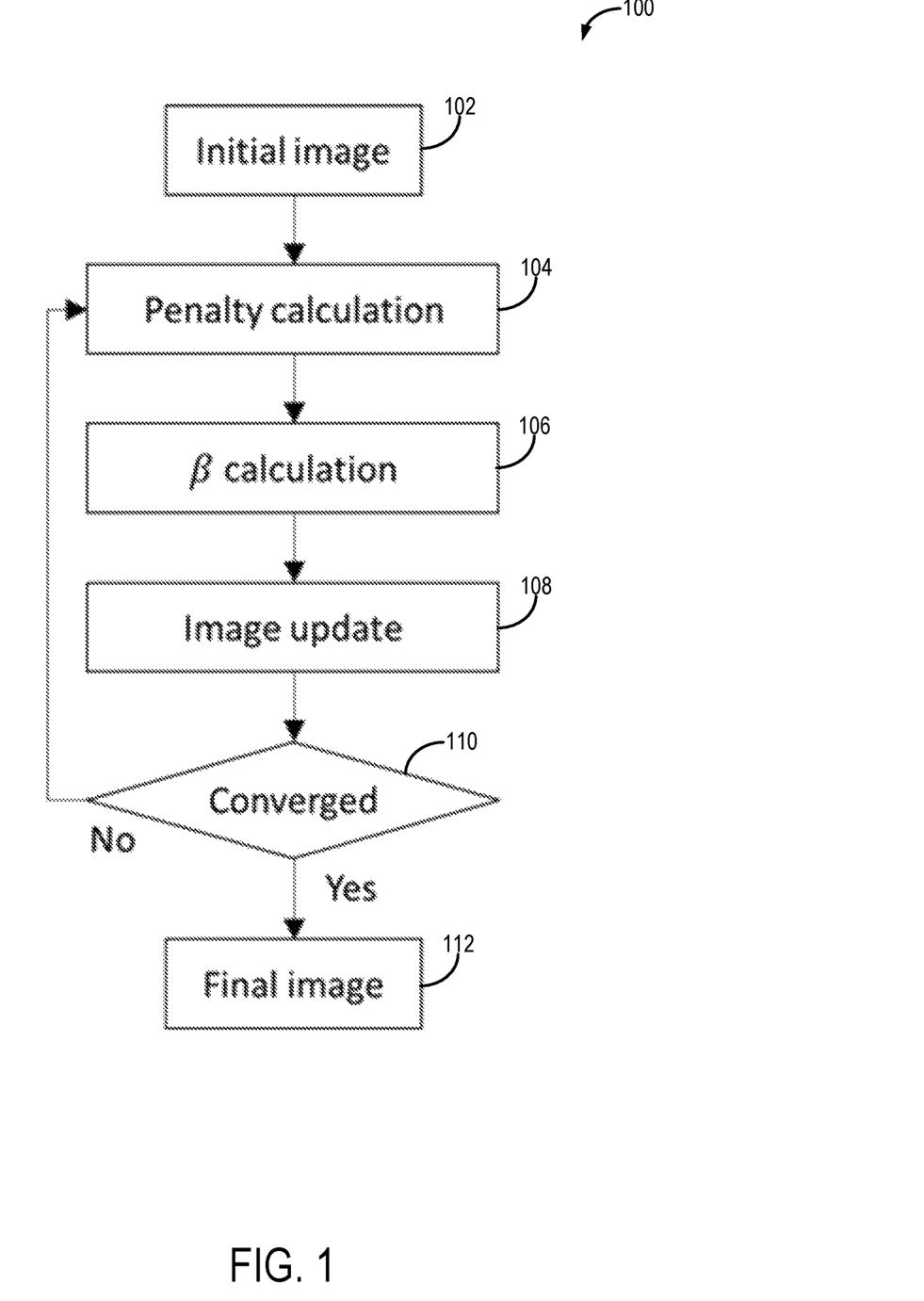
FIG. 1 is a flowchart setting forth steps of a process, in accordance with aspects of the present disclosure.

Turning to FIG. 1, a flowchart setting forth non-limiting examples steps of a process 100 in accordance with aspects of the present disclosure is provided. The process 100 may be carried out using a system as described with reference to FIG. 2, or any of a variety of other tomographic imaging system. Specifically, the process 100 may begin at process block 102 with acquiring or accessing an initial image. The initial image may be a filtered back-projection image or a small constant image. Example initial images include CT, SPECT, PET, MR, US, optical and other image types. Then, at process block 104, a penalty calculation is performed, in accordance with Eqn. 1. In some aspects, a quadratic, total variation, or non-local function, as well as other differentiable penalty functions, can be used in the calculation. In many penalty functions, such as total variation and non-local penalties, there exist additional hyper-parameters inside of penalty function. These parameters may be estimated before each iteration.

Then, at process block 106, a hyper-parameter calculation may be performed, as described above. In some aspects, a hyper-parameter image, or β image, may be generated at process block 106. Then, at process block 108, the image may be updated, using the following update equation:

$$x^{n+1} = x^n - \left(\Delta x + \beta \odot \frac{\Psi(x)}{\dot{\Psi}(x)}\right) / (1 + \beta), \quad (9);$$

where $$\Delta x \left(= \frac{\dot{L}(x)}{\ddot{L}(x)}\right)$$

can be various update types: (a) EM, (b) SQS, (c) SART and (d) weighted least square, as follows:

$$\Delta x_j = x_j \frac{\sum_{i=1}^{M} a_{ij}\left(1 - y_i / \sum_{j'=1}^{N} a_{ij'}x_{j'}\right)}{\sum_{i=1}^{M} a_{ij}}; \quad (10a)$$

$$\Delta x_j = \frac{\sum_{i=1}^{M} a_{ij}\left(1 - y_i / \sum_{j'=1}^{N} a_{ij'}x_{j'}\right)}{\sum_{i=1}^{M} a_{ij}\left(y_i / \left(\sum_{j'=1}^{N} a_{ij'}x_{j'}\right)^2\right)}; \quad (10b)$$

$$\Delta x_j = \frac{\sum_{i=1}^{M} a_{ij}\left(\sum_{j'=1}^{N} a_{ij'}x_{j'} - y_i\right)}{\sum_{i=1}^{M} a_{ij}\left(\sum_{j'=1}^{N} a_{ij'}\right)}; \text{ and} \quad (10c)$$

$$\Delta x_j = \frac{\sum_{i=1}^{M} a_{ij}w_i\left(\sum_{j'=1}^{N} a_{ij'}x_{j'} - y_i\right)}{\sum_{i=1}^{M} a_{ij}w_i\left(\sum_{j'=1}^{N} a_{ij'}\right)}. \quad (10d)$$

Here, $\Sigma_{j'=1}^{N} a_{ij'}$ is the projection and $\Sigma_{i=1}^{NM} a_{ij}$ is the back-projection. N is the number of image voxels and M is the number of measurement. Also, n is the number of iterations. In some aspects, subsets of measurements can be used.

Then, at decision block 110, a stopping criterion is evaluated. For instance, a condition of convergence may be to determine whether to continue or determine the final image, as indicated by process block 112. In particular, a condition of convergence may be met if $|x^n - x^{n-1}|_2 < \epsilon$, where $\epsilon$ is a small constant.

Figure 2:
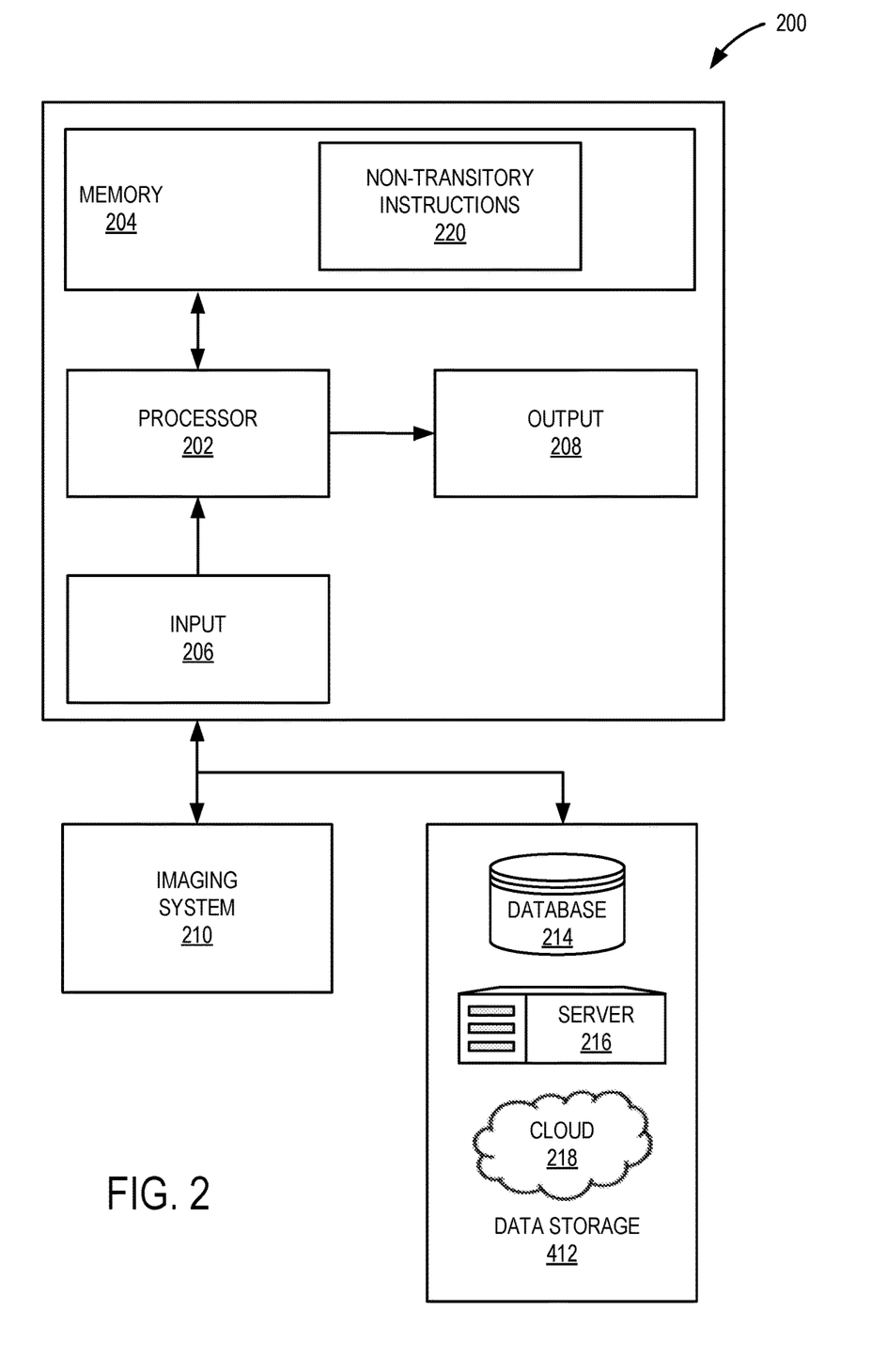
FIG. 2 is a schematic diagram of an example system, in accordance with aspects of the present disclosure.

Turning now to FIG. 2, a block diagram of a system 200 in accordance with aspects of the present disclosure is shown. In some configurations, the system 200 can include a processor 202, a memory 204, an input 206, an output 208, and may be configured to carry out steps, in accordance with the method described herein. In general, the system 200 may be any device, apparatus or system configured for carrying out instructions for, and may operate as part of, or in collaboration with a computer, system, device, machine, mainframe, or server. In this regard, the system 200 may be a system that is designed to integrate with a variety of software and hardware capabilities and functionalities, and may be capable of operating autonomously. In some aspects, the system 200 may be portable, such as a mobile device, tablet, or other portable device or apparatus.

As shown in FIG. 2, in some configurations, the system 200 may be in communication with an imaging system 210, allowing access via input 206 to imaging, and other information, by way of wired or wireless connection or communication system. The imaging system 210 may include any tomographic imaging systems or devices such as computed tomography (CT) systems, such as cone-beam CT, dual energy CT, and spectral CT systems, single photon emission computed tomography (SPECT) systems, positron emission tomography (PET) systems, such as static PET, dynamic PET, and time-of-flight PET systems, magnetic resonance imaging (MR) systems, ultrasound (US) systems, tomosynthesis systems, fluoroscopy systems, optical imaging systems, and other imaging systems. Although shown in FIG. 2 as separate from the imaging system 210, in some implementations, system 200 maybe part of the imaging system 210.

In addition to being configured to carry out steps for operating the system 200 using instructions stored in the memory 204, the processor 202 may also be configured to receive, access and process imaging data, and other data, as described. In some aspects, the processor 202 may also be configured to control the imaging system 210 to acquire imaging data, and images. To this end, the processor 202 may execute non-transitory instructions 220, stored in memory 204 in the form of non-transitory computer-readable media, as shown in FIG. 2.

In some implementations, the system 200 may also be in communication with an external data storage 212 that may include a database 214, a server 216, or a cloud 218, and so forth, as shown in FIG. 2. In this manner, imaging data, such as CT, PET, SPECT, MRI, and other data, may be retrieved and processed, in accordance with aspects of the disclosure.

Figure 3:
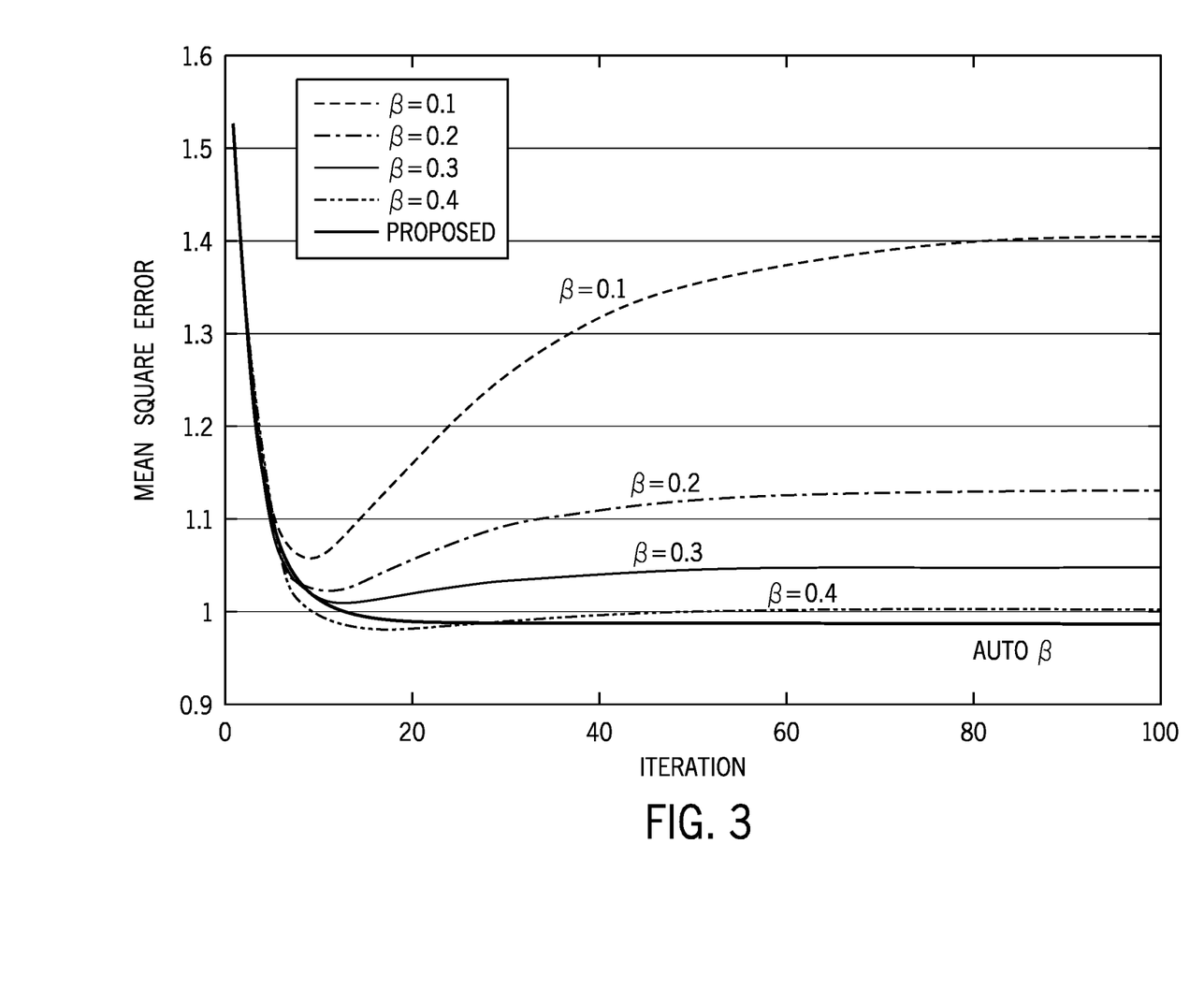
FIG. 3 is a graph comparing mean square error of a conventional reconstruction technique in comparison with the method of the present disclosure.
Figure 4:
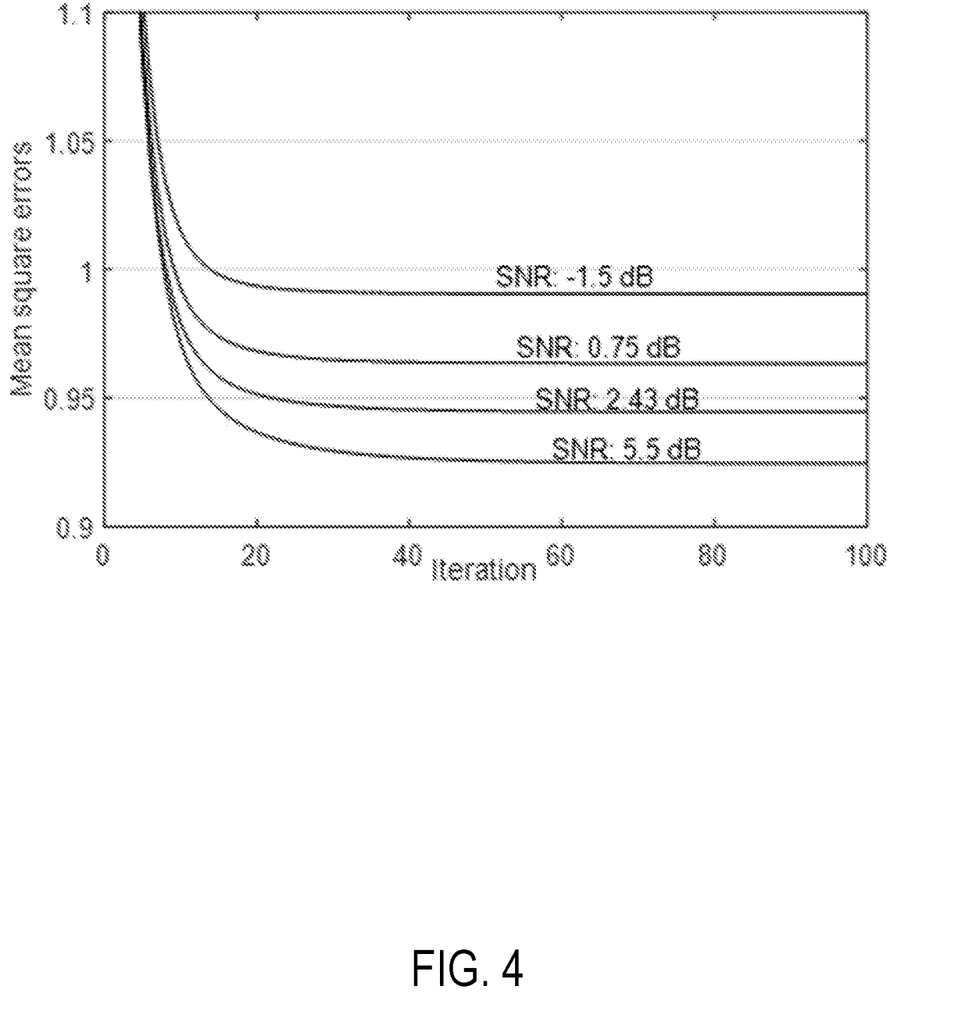
FIG. 4 is a graph illustrating convergence as a function of various noise levels, in accordance with aspects of the present disclosure.
Figure 5:
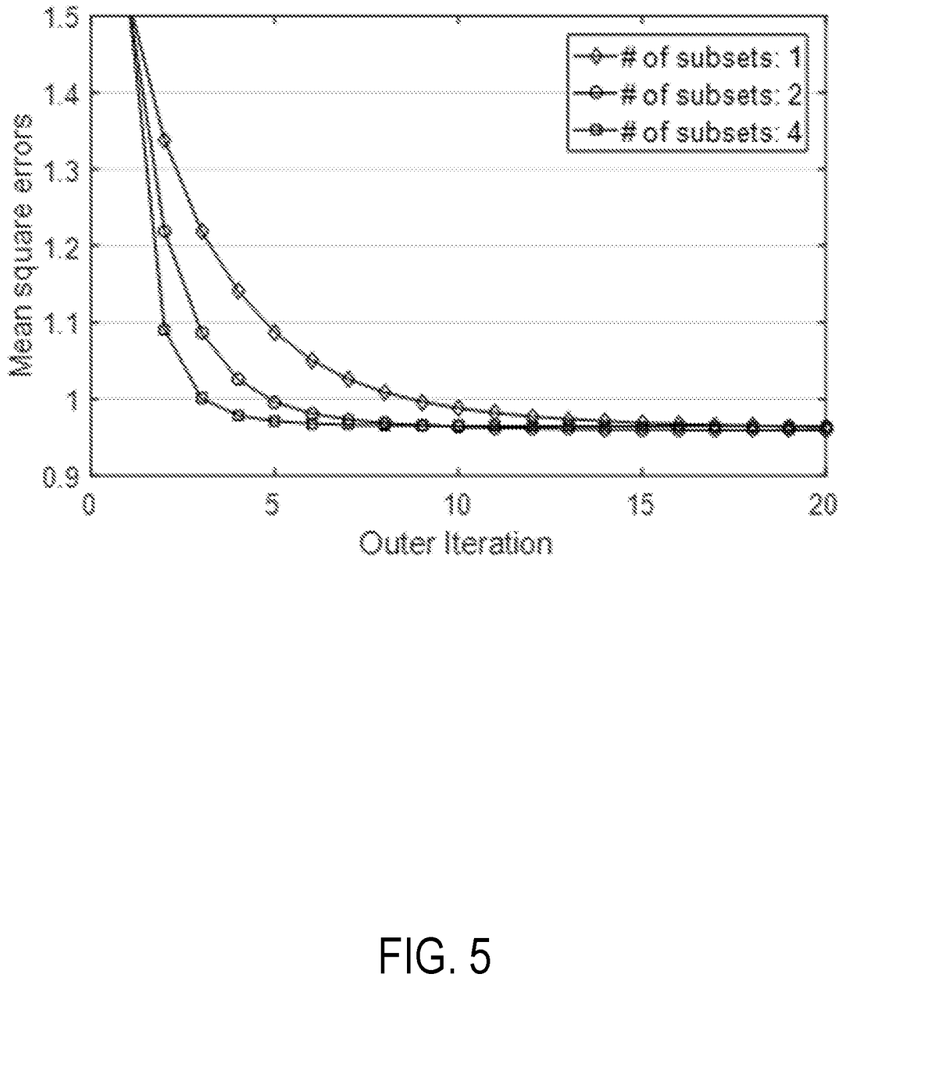
FIG. 5 is a graph illustrating convergence as a function of various subsets, in accordance with aspects of the present disclosure.
Figure 6:
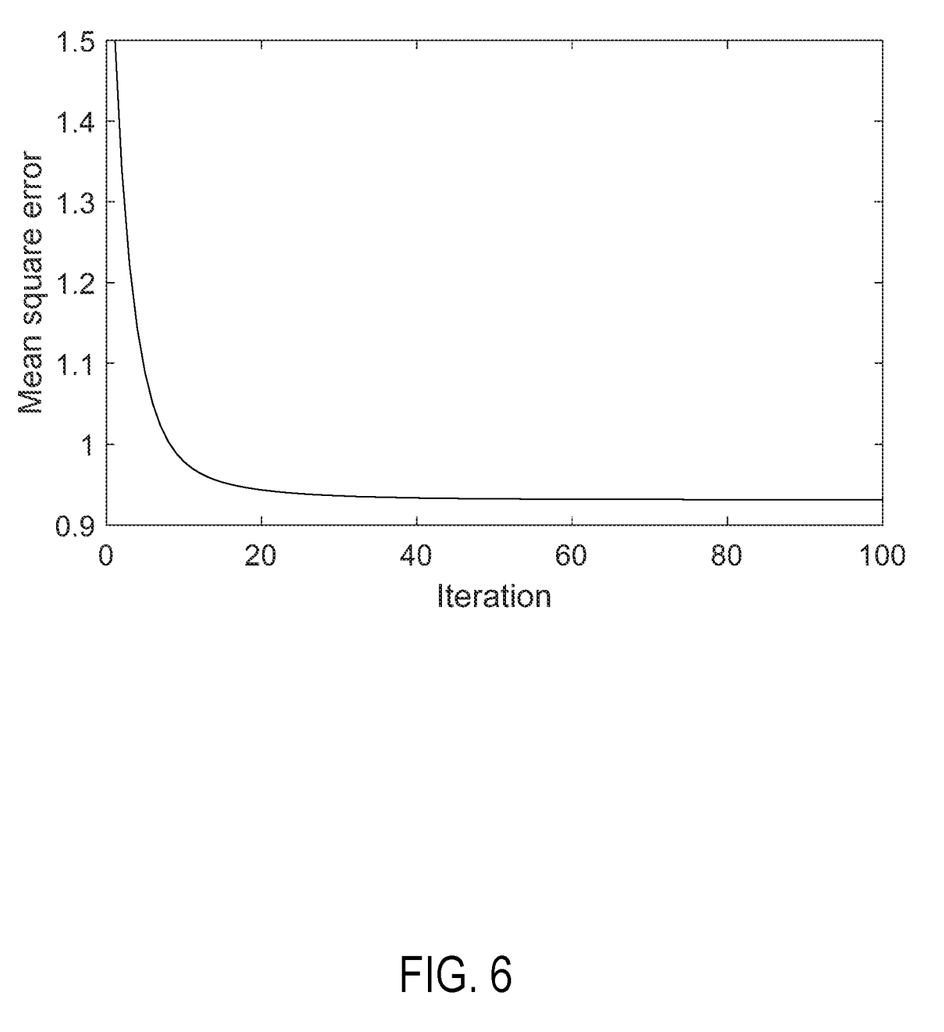
FIG. 6 is a graph illustrating convergence using total variation, in accordance with aspects of the present disclosure.

To elucidate features of the present method, a comparison with a conventional fixed beta was performed, as described with reference to Eqn. (1). In this experiment, a quadratic penalty that did not have additional tuning hyper-parameter was used. As appreciated from FIG. 3, small betas in the conventional method show divergence. By contrast, the present auto-beta selection approach converges clearly. In another example, the present approach was utilized using different noise levels, with Poisson noise being imposed. As appreciated from FIG. 4, in all cases, the proposed approach converges. In yet another example, experiments were performed using different number of subsets, as shown in FIG. 5. In this figure, the x-axis represents the outer iteration, and shows convergence with subsets. FIG. 6 shows a further example of convergence using a total variation function that is one of the most popular penalty functions. As appreciated from these examples, convergence can be achieved using various imaging conditions.

The present invention has been described in terms of one or more preferred embodiments, and it should be appreciated that many equivalents, alternatives, variations, and modifications, aside from those expressly stated, are possible and within the scope of the invention.

What is claimed is:

1. A method for generating an image using a tomographic imaging system, the method comprising:
   a) receiving an initial image acquired from a subject using the tomographic imaging system;
   b) performing, using the initial image and a cost function model, a penalty calculation based on a spatially variant hyper-parameter;
   c) generating an updated image using the penalty calculation;
   d) generating a finalized image by iteratively repeating steps b) and c) until a stopping criterion is met; and
   wherein method further comprises calculating an update term as follows:

$$x^{n+1} = x^n - \left(\frac{\dot{L}(x)}{\ddot{L}(x)} + \beta\frac{\Psi(x)}{\dot{\Psi}(x)}\right) / (1+\beta);$$

where $x^n$ is an initial image, $x^{n+1}$ is an updated image, L(x; y) is a log-likelihood function, and $\psi(x)$ is a penalty function.

2. The method of claim 1, wherein the method further comprises acquiring, using the tomographic imaging system, a plurality of images of the subject.

3. The method of claim 1, wherein the tomographic imaging system includes a computed tomography (CT) system, a single photon emission computed tomography (SPECT) system, a positron emission tomography (PET) system, a magnetic resonance imaging (MR) system, an ultrasound (US) system, a tomosynthesis system, a fluoroscopy system, or an optical imaging system.

4. The method of claim 1, wherein the initial image comprises one of a filtered back-projection image or a constant image.

5. The method of claim 1, wherein the penalty function comprises one of a quadratic, a total variation, a non-local, a sparse or a rank penalty function.

6. A method for generating an image using a tomographic imaging system, the method comprising:

a) receiving an initial image acquired from a subject using the tomographic imaging system;
b) performing, using the initial image and a cost function model, a penalty calculation based on a spatially variant hyper-parameter;
c) generating an updated image using the penalty calculation;
d) generating a finalized image by iteratively repeating steps b) and c) until a stopping criterion is met; and
further comprising generating a hyper-parameter image according to:

$$\beta_j = \frac{\sum_{i=1}^{M} a_{ij}\left(1 - \frac{y_i}{\bar{y}_i}\right)^2 \left(\sum_{j'=1}^{N} a_{ij'}\right)}{\sum_{i=1}^{M} a_{ij}\left(\sum_{j'=1}^{N} a_{ij'}\right)}$$

7. The method of claim 1, wherein $$\frac{\dot{L}(x)}{\ddot{L}(x)}$$

is obtained using an EM algorithm, an SQS algorithm, a SART algorithm, or a weighted least squares algorithm.

8. The method of claim 1, wherein the method further comprises using a subset technique.

9. A system for reconstructing a tomographic image of a subject, the system comprising:
   an input configured to receive a plurality of images acquired from a subject using a tomographic imaging system;
   at least one processor configured to:
      a) receive an initial image acquired from a subject;
      b) perform, using the initial image and a cost function model, a penalty calculation based on a spatially variant hyper-parameter;
      c) generate an updated image using the penalty calculation;
      d) generate a finalized image by iteratively repeating steps b) and c) until a stopping criterion is met;
   wherein the processor is further configured to generate a hyper-parameter image according $$\beta_j = \frac{\sum_{i=1}^{M} a_{ij}\left(1 - \frac{y_i}{\bar{y}_i}\right)^2 \left(\sum_{j'=1}^{N} a_{ij'}\right)}{\sum_{i=1}^{M} a_{ij}\left(\sum_{j'=1}^{N} a_{ij'}\right)};$$

and
   an output for at least displaying the finalized image.

10. The system of claim 9, wherein the tomographic imaging system includes a computed tomography (CT) system, a single photon emission computed tomography (SPECT) system, a positron emission tomography (PET) system, a magnetic resonance imaging (MR) system, an ultrasound (US) system, a tomosynthesis system, a fluoroscopy system, or an optical imaging system.

11. The system of claim 9, wherein the initial image comprises one of a filtered back-projection image or a constant image.

12. The system of claim 9, wherein the penalty function comprises one of a quadratic, a total variation, a non-local, a sparse or a rank penalty function.

13. The system of claim 9, wherein the processor is further configured to calculate an update term as follows:

$$x^{n+1} = x^n - \left(\frac{\dot{L}(x)}{\ddot{L}(x)} + \beta\frac{\dot{\psi}(x)}{\ddot{\psi}(x)}\right) \Big/ (1+\beta);$$

where $x^n$ an initial image, $x^{n+1}$ is an updated image, L(x; y) is a log-likelihood function, and $\psi(x)$ is a penalty function.

14. The system of claim 13, wherein $$\frac{\dot{L}(x)}{\ddot{L}(x)}$$

is obtained using an EM algorithm, an SQS algorithm, a SART algorithm, or a weighted least squares algorithm.

15. A method for generating an image using a tomographic imaging system, the method comprising:
 a) receiving an initial image acquired from a subject using the tomographic imaging system and generating a spatially variant hyper-parameter based on a quantity of noise in the initial image;
 b) performing, using the initial image and a cost function model, a penalty calculation based on the spatially variant hyper-parameter;
 c) generating an updated image using the penalty calculation;
 d) generating a finalized image by iteratively repeating steps b) and c) until a stopping criterion is met; and
 wherein the method further comprises calculating an update term as follows;

$$x^{n+1} = x^n - \left(\frac{L(x)}{\ddot{L}(x)} + \beta\frac{\psi(x)}{\ddot{\psi}(x)}\right) \Big/ (1+\beta);$$

where $x^n$ is an initial image, $x^{n+1}$ is an updated image, L(x; y) is a log-likelihood function, and $\psi(x)$ is a penalty function.

* * * * *